United States Patent [19]
Wardlaw

[11] Patent Number: 6,127,184
[45] Date of Patent: Oct. 3, 2000

[54] CALIBRATION OF A WHOLE BLOOD SAMPLE ANALYZER

[75] Inventor: Stephen C. Wardlaw, Old Saybrook, Conn.

[73] Assignees: Robert A. Levine, Guilford; Wardlaw Partners, LP, Lyme, both of Conn.

[21] Appl. No.: 09/248,135

[22] Filed: Feb. 10, 1999

Related U.S. Application Data

[60] Provisional application No. 60/077,198, Mar. 7, 1998.

[51] Int. Cl.⁷ .................................................... G01N 21/03
[52] U.S. Cl. .............................. 436/50; 436/8; 436/165; 422/67; 422/82.05; 422/102; 356/244; 356/246; 356/440
[58] Field of Search .................................. 436/43, 46, 50, 436/63, 66, 69, 165, 70, 8; 422/63, 67, 73, 82.05, 82.09, 102, 119; 356/244, 246, 440

[56] References Cited

U.S. PATENT DOCUMENTS

| | | | |
|---|---|---|---|
| 4,790,640 | 12/1988 | Nason | 350/534 |
| 4,950,455 | 8/1990 | Smith | 422/56 |
| 5,132,097 | 7/1992 | Van Deusen et al. | 422/82.09 |
| 5,293,426 | 3/1994 | Wouch et al. | 382/1 |
| 5,427,959 | 6/1995 | Nishimura et al. | 436/534 |
| 5,541,064 | 7/1996 | Bacus et al. | 435/6 |
| 5,547,849 | 8/1996 | Baer et al. | 356/244 |
| 5,837,546 | 7/1992 | Allen et al. | 436/169 |

*Primary Examiner*—Long V. Le
*Attorney, Agent, or Firm*—William W. Jones

[57] ABSTRACT

Formed constituents of a quiescent anticoagulated whole blood or other biologic fluid sample are optically analyzed by an optical scanning instrument. The sample is contained in a sample chamber that has a varying through plane thickness. The thickness of any fields of view in the blood sample which contain plasma lacunae can be calculated by the instrument as a function of signal emission strength emanating from the colored plasma in the lacunae. The signal emissions can be the result of sample fluorescence or can be the result of signal density emanating from the sample. Particle volumes can be measured as a function of signal emission suppression which is caused by formed particles in the blood sample. The scanning instrument is calibrated by means of the inclusion of a calibration area associated with the chamber which calibration area includes a portion which receives a known depth of colored plasma from the blood sample, and which calibration area also includes a colorant-emission-suppressing feature which feature has a known volume. The scanning instrument scans the known depth portion of the calibration area to determine what degree of signal emission strength correlates to the known depth, and the scanning instrument also scans the colorant-emission-suppressing feature to determine what degree of signal suppression correlates to the known volume of the aforesaid feature. The instrument stores the information gained from the calibration area and then proceeds to analyze the blood sample for formed constituent volumes and constituent counts per unit of the blood sample.

10 Claims, 3 Drawing Sheets

CALIBRATION OF A WHOLE BLOOD SAMPLE ANALYZER

This application claims benefit of provisional application 60/077,198, filed Mar. 7, 1998.

TECHNICAL FIELD

This invention relates to an apparatus and method for analyzing a blood or other biologic fluid sample in a quiescent state, within a preferably disposable container, without the need for fluid streams passing through the blood sample analysis apparatus during the analytic process, whereby blood constituent counts per unit volume of sample and measurement of blood constituent volumes can be performed using an optical scanning instrument. More particularly, this invention relates to a method and apparatus for calibrating the analytical system for each use of said system.

BACKGROUND ART

Recent advances in biological fluid analysis, and in particular, analytical hematology have increased the quantity and quality of information available from a patients blood sample. As a result, the medical community's interest in using patients blood samples as a diagnostic tool has also increased, and the most common test that is performed on anticoagulated whole blood is the complete blood count, or CBC, which is a suite of tests which are considered to include measurements of the hematocrit (Hct), hemoglobin (Hgb), red blood cell count (RBC). white blood cell count (WBC) and platelet count (Plt), red blood cell metrics such as the mean cell volume (MCV) and others, as well as the leukocyte differential count (LDC or "Diff") which is the classification of the types of white blood cells present. Compared to any other laboratory test, it is a peculiar characteristic of the CBC, that any instrument or method which performs it must do four different types of analyses. First, the general physical properties of the sample, namely the hematocrit and various cell or particle counts must be analyzed using quantitative methods relating to the entire sample. In conventional instrumentation and methods, this requires accurate sample metering and dilution, followed by specialized measurement apparatus. Secondly, a specific chemical property of the sample, namely the hemoglobin concentration, must be measured, usually by quantitative chemical means. Thirdly, the instrument must measure quantitative aspects of the individual cells, which usually involves providing a high dilution of the sample with a subsequent passage of the diluted material through a flow cell which measures the cells using electrical or optical means. Fourthly, qualitative measurements are used to classify the percentage of the total white blood cells which are composed of specific sub-populations. The number of sub-populations depends upon the sophistication of the instrument involved, which may be as little as two or more than seven classifications.

Historically, the different aspects of the CBC have been performed using separate methods. For example, the LDC portion of a CBC was traditionally performed by smearing a small amount of undilute blood on a slide, staining it, and examining the smear under a microscope. Reasonable results can be gained from such a smear, but the accuracy and reliability of the data depends largely on the technician's experience and technique. In addition, the use of blood smears is labor intensive and cost prohibitive, and is therefore generally not favored for commercial applications.

Another method uses electrical impedance or optical flow cytometry. Flow cytometry involves passing a diluted blood sample through a small vessel wherein electrical impedance or optical sensors can evaluate the constituent cells as they pass serially through the vessel. The same apparatus may also be used to simultaneously enumerate and provide cell metric data. To evaluate WBC's and/or platelets, the blood sample must be diluted, and the sample must be treated to mitigate the overwhelming number of the RBC's relative to the WBC's and the platelets. Although more expedient and consistent than the above described smear methods, flow cytometry also possesses several disadvantages. One disadvantage of flow cytometry is the plumbing and fluid controls that are necessary for controlling the flow rate of the diluted blood sample past the sensors, The plumbing in current flow cytometers can, and often does, leak, thus potentially compromising the accuracy and the safety of the equipment. Another disadvantage of many current flow cytometers relates to the accuracy of the internal fluid flow controls and automated dilution equipment. The accuracy of the flow cytometer depends upon the accuracy of the fluid flow controls and the sample dilution equipment, and their ability to remain accurately calibrated. Flow controls and dilution equipment require periodic recalibration. The need for recalibration illustrates the potential for inaccurate results and the undesirable operating costs that exist with many presently available flow cytometers. An article authored by John L. Haynes, and published in Cytometry Supplement 3: 7–17 in 1988 describes the principles of flow cytometry, both impedance and optical, and the application of such a technology to various fields of endeavor. Blood samples being examined in flow cytometers are diluted anywhere from 10:1 to 50,000:1.

Another approach to cellular analysis is volumetric capillary scanning as outlined in U.S. Pat. Nos. 5,547,849; 5,585,246 and others, wherein a relatively undiluted sample of whole blood is placed into a capillary of known volume and thickness and is examined while the blood is in a quiescent state. This technique deals with the presence of the red blood cells by limiting the scanning wavelengths to those to which the red blood cells are relatively transparent, and it requires that the sample be treated so that the red blood cells do not aggregate during the measurement process. Thus, this technique is limited to the use of longer wavelength fluorescence, and there is no provision for the examination of red blood cells and platelets or the examination of any cellular morphology. Also, because the counts must occur in a constant volume, it is difficult or impossible to examine a wide range of sample particulate constituents in a single sample vessel, since the relative numbers of these constituents can vary over a thousand to one in a whole blood sample. There are a number of commercial instruments available for performing a CBC or related tests, but those which provide more than a few of the CBC tests quickly become complex, expensive and prone to malfunction. In addition, there are a number of methods proposed for specific hematological tests, but these do not provide all of the clinically useful information which is expected in a CBC.

Another problem with the more complex currently available instruments for performing CBC's is that they must be calibrated. This is because most of the dilutions and measurements are relative rather than absolute, so in order to provide exact quantitation, actual particulates, generally stabilized samples of whole blood with known values, must be analyzed by the instruments, and the instrument adjusted so that the correct values are produced. It should be obvious that this type of calibration is prone to errors in the preparation of the standard material and its stability during transportation and storage. The standard material is also expensive, which increases the cost of the tests.

In a co-pending U.S. patent application Ser. No. 09/249,721, a method is disclosed which allows the measurement of many important blood parameters within a quiescent layer of substantially undiluted whole blood. An important feature of the said invention is the lack of need for any external calibration material, but to be optimally accurate, it requires a means of accurately ensuring the dimensional accuracy of the chambers of the described device.

It would be desirable to have a method and apparatus for examining a quiescent sample of anticoagulated whole blood, which method and apparatus are capable of providing accurate qualitative and quantitative results on a number of different hematologic parameters, and does not require sample fluid flow through the sampling chamber during sample analysis. It would be desirable to provide such a method and apparatus which could derive volumetric blood cell counts and cell volume information from the quiescent blood sample and did not require external materials for its calibration.

DISCLOSURE OF THE INVENTION

This invention relates to a method and apparatus for use in examining and obtaining information from a quiescent substantially undiluted anticoagulated whole blood sample which is contained in a chamber. The phrase "substantially undiluted" as used in connection with this invention describes a blood sample which is diluted by no more than about 1:1, and preferably much less. Generally the only reagents that will be used in performing the method of this invention are dyes, stains and anticoagulants, and these reagents, even if liquid, are not designed to dilute the specimen. Preferably, the varying through plane thicknesses of the several regions in the chamber will create sufficient capillary forces in all regions of the chamber so as to cause spreading of the blood sample throughout the chamber which ultimately results in a quiescent blood sample in the chamber. The only motion in the blood sample at the time of analysis will be Brownian motion of the blood sample's formed constituents, which motion is not disabling of the use of the device of this invention. The apparatus includes a sample-holding chamber which has opposite sample-containment walls, at least one of which is transparent, which walls converge in at least one portion of the chamber. The through plane thickness of the chamber thus varies in different regions of the chamber. As used in this disclosure, the phrase "through plane" refers to a line of sight which corresponds to the shortest distance between the convergent walls in any region of the chamber. The degree of convergence of the two walls, i.e., the distance between the two walls, at any particular point in the chamber is either known, or it can be measured after the sample has been placed in the chamber, as will be described hereinafter. This method and apparatus are more fully described in co-pending U.S. patent application Ser. No. 09/249,721.

Traditionally, when cells in a biologic fluid are enumerated or otherwise quantitatively measured in a standard blood cell counting chamber, commonly known as a hemocytometer, it is well known that minute errors in forming the cover glass, cleaning the surfaces or filling the chamber have a substantial effect on the accuracy of the measurement because small dimensional errors in the height of the chamber, which is nominally $100\mu$, have a large effect on any observed volume within the chamber. These chambers use blood diluted from 1:10 to 1:1000. In the case of the above-described invention, the chamber vertical dimensions are much smaller than in a standard chamber, generally in the range of about $2\mu$ to $40\mu$, which places extreme requirements on the dimensional accuracy of the chamber. Although it is possible to manufacture chambers with the required dimensional tolerances, it is more practical, particularly in the case of a disposable chamber, to build the chamber to an approximate tolerance and then to measure the actual chamber height, or volume, in each field of interest.

The thinnest region in the chamber will be sized so that a monolayer of individual red blood cells or other particles present in the sample will form when the chamber is filled with the sample. The thickness of this part of the chamber should be between two and seven microns, and is preferably about five microns. Thus measurements of the individual red cells, metrics such as the mean red cell volume (MCV) and mean corpuscular hemoglobin (MCH) can be measured in this area of the chamber, as will be described hereinafter. Because volumetric measurements of the cells will be performed in this region, the volume, or chamber height, in any given field of view must be known to an appropriate degree of accuracy, which is preferably at least +/−5%.

From the thin portion of the chamber, the chamber thickness increases so as to form progressively thicker regions in the chamber that are used to identify and enumerate other cellular or particulate elements in the blood sample. In all cases, such enumeration will occur in a region of the chamber where the thickness of the region can be determined, so that the cell or constituent counts can be given as a number of cells or constituents in a given volume of the sample. The thickness of the chamber in this region thereof is typically in the range of between about seven to about forty microns. The chamber is contained in a sample holder into which the sample can be drawn. Details of such a sample holder are disclosed in co-pending U.S. patent application Attorney's Docket No. UFB-006. Because enumeration of the cells or particulates per unit volume of fluid is determined here, the volume, or chamber height, in any given field of view must be known to an appropriate degree of accuracy, which is generally within +/−5% or preferably +/−3% or better.

The sample to be assayed is admixed with a colorant which can be, for example, a fluorescent dye, and the resultant admixture spreads out in the chamber so as to form a quiescent sample that has a varying thickness due to the convergence of the walls of the chamber. The colorant can be added to the sample prior to admission of the sample into the chamber, or the colorant can be added to the sample while the sample is within the confines of the chamber, such as by dry coating the colorant on walls of the chamber. Regions of interest in the chamber are selectively illuminated by a light source having a selected wavelength, or wavelengths, which causes the colorant in the sample to fluoresce, or otherwise be quantitated. Regions in the chamber containing the various sized formed constituents in the sample are thus scanned, preferably by an optical instrument, and the results of the scans may be digitized and analyzed by the scanning instrument. In the case of whole blood, the sample will be manipulated or treated to ensure that there will be regions in the sample which do not contain formed constituents, and only contain the plasma portion of the blood sample in which cells or other formed constituents in the blood are suspended.

The magnitude per unit area of the emitted fluorescent or transmitted signal (optical density) in such formed constituent-free regions is mathematically related to the thickness of the plasma, therefore the degree of fluorescence or the optical density of the plasma increases as the thickness of the chamber increases. Likewise, the degree of fluorescence or optical density from the sample will diminish in proportion to the volume of any formed bodies in the blood sample which are operable to displace the colorant which is dissolved in the plasma. Therefore, if an absolute relationship can be established between any given signal magnitude and a volume (or chamber height at some established field area), in any region of the chamber or in an adjacent chamber, the exact volume or chamber height can be determined for any area of observation as long as there are sufficient areas containing plasma lacunae which are free of interfering formed constituent matter, and the concentration of the colorant is identical between the calibration area and the measured area. Once the calibration area is scanned and the colorant signal therefrom is measured, the scanning instrument will know that a chamber thickness "A" emits colorant signal "B", and also that fractions or multiples of "B" will equal proportional fractions or multiples of "A". With this information, the number of formed constituents per unit volume of sample can be counted since the area of any field of view of the scanning instrument will be known. By multiplying the known area of the field of view times the measured thickness of the field of view, the volume of the field of view can be calculated anywhere in the chamber where a clear plasma area of the blood sample exists. The difficulty lies in obtaining the calibration information for the particular sample.

In an article by Diether Rectenwald et al, *J. Phys Chem*: Vol 97, #12, 1993, pages 2868–2870, a method is shown whereby spherical beads are introduced into a chamber and the colorant per volume calculated by measuring the reduction of the colorant signal by the beads, since the beads displace the colorant. The volume of the beads themselves are measured by the digital camera used in the experiment.

However, for the application of the current invention, the beads are not effective because the beads and the blood cells mutually interfere in each other's measurement. It is therefore desirable to have a volume colorant calibration means which can be used in the presence of blood cells or other particulates.

It is therefore an object of this invention to provide a method and apparatus for use in obtaining volumetrically related information from a quiescent anticoagulated whole blood sample.

It is an additional object of this invention to provide a method and apparatus of the characterized wherein said volumetrically related information can be obtained without the need to employ external standardization substances.

It is an additional object of this invention to provide a method and apparatus of the character described which allows a substantially undiluted whole blood sample or other biologic fluid to be examined for formed constituent enumeration-per-unit-sample-volume information.

It is a further object of this invention to provide a method and apparatus of the character described which includes a sample-containing chamber which has different through plane thickness regions that are formed by opposed convergent chamber walls, at least one of which walls is transparent so that the sample can be examined through the transparent wall either optically or visually.

It is another object of this invention to provide a method and apparatus of the character described wherein the various through plane thickness regions in the chamber are sized so as to enable determination of morphologic characteristics, counts, and volumes of different size individual cells and other formed components in the fluid sample.

It is an additional object of this invention to provide a method and apparatus for use in calibrating a scanning instrument in order to enable the instrument to determine the volumes of selected fields of view in the sample, and to enable the instrument to measure formed constituent volumes in the sample.

BRIEF DESCRIPTION OF THE DRAWINGS

These and other objects and advantages of the invention will become more readily apparent from the following detailed description of several embodiments of the invention when taken in conjunction with the accompanying drawings in which.

DETAILED DESCRIPTION OF SPECIFIC EMBODIMENTS OF THE INVENTION

Figure 1:
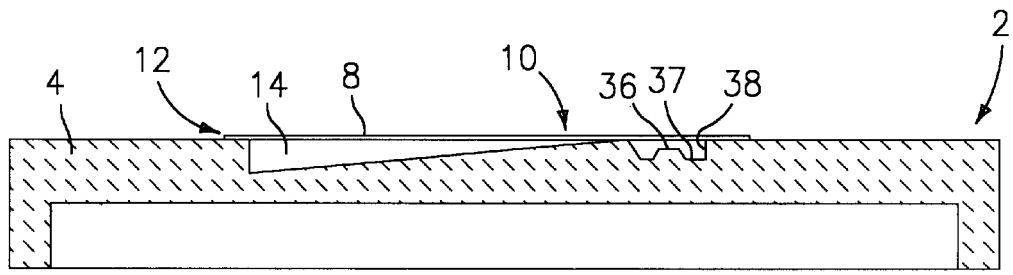
FIG. 1 is a cross sectional view of one embodiment of a sample chamber which has a through plane thickness that varies in different X, Y regions of the chamber, and which chamber has a first embodiment of an instrument calibration area associated with it.
Figure 2:
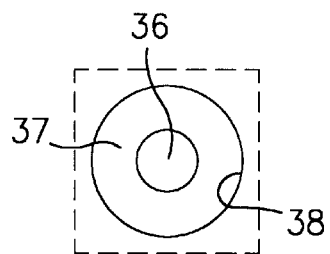
FIG. 2 is a plan view of the instrument-calibration area of FIG. 1.

Referring now to the drawings, FIG. 1 is a cross sectional view of a device which is denoted generally by the numeral 2, which device 2 includes a sample-containing chamber 14 that has a varying through plane thickness. The device 2 includes a lower support wall 4, and an upper wall 8, which for illustrative purposes may be a microscope slide cover slip. At least one of the walls 4 and 8 must be transparent so that a sample disposed therebetween can be examined through the transparent wall 4 or 8. If so desired, both of the walls 4 and 8 can be transparent. The wall 8 has one edge 10 which is proximal to the thinnest through plane region of the chamber 14, and an opposite edge 12 which is proximal to the thickest through plane region of the chamber 14. Co-pending U.S. patent application Ser. No. 09/249,721 describes many variations of the varying thickness chamber 14.

Calibration of the scanning instrument can be accomplished as follows. One calibration feature which may be incorporated into the device 2 includes a molded calibration-standard area 38 which is adjacent to, and in fluid communication with the narrow end 10 of the chamber 14. When the colorant and sample mixture enters the chamber 14, the calibration standard area 38 will fill up with the stained fluid component of the sample. The calibration area 38 can take the form of a well of accurately controlled depth which has a bottom floor 37, and a central protuberance 36 that extends upwardly from the floor 37, and which protuberance 36 has an accurately know volume. It will be appreciated that the geometric feature 36 could take the form of dimple of accurately known volume. A protuberance will suppress the signal emanating from the feature 36 to a degree which is proportional to the volume of the protuberance, and a dimple will enhance the signal emanating from the feature 36 to a degree which is proportional to the volume of the dimple. Thus the distance between the floor 37 and the undersurface 7 of the chamber wall 8 is known; and the volume of the feature 36 is also known and communicated to the scanning instrument at the start of the scan.

Before the scanning instrument begins a sample analyzing procedure, it first goes to the area 38 and creates an intensity map of the area 38. The instrument then calculates the average intensity from the floor 37 of the area scanned. This average value, when multiplied times the number of pixels in the area 38 gives a value S1, which is the intensity which would occur from area 38 if it were not for the presence of the protuberance 36. A second value, S2, is created by summing the intensity of all of the pixels in the area 38. Therefore, the difference, S1–S2 represents the signal produced by the volume of the fluid displaced by the protuberance. The actual volume V of the protuberance is encoded in a machine readable bar code or other label which is placed on the device 2 and scanned by the scanning instrument. The scanning instrument can use this [(S1–S2)/V] value to calculate the volume of any formed components in the chamber 14 or the volume of any part of the chamber itself. The scanning instrument will thus be provided with accurately calibrated chamber region field of view volumetric information; and formed constituent volumetric information for the particular colorant and device 2 that the instrument is examining. It should be noted that although a protuberance is shown, a declivity could be used as well, as could any identifiable feature whose volume, or volume per unit area is known.

Figure 3:
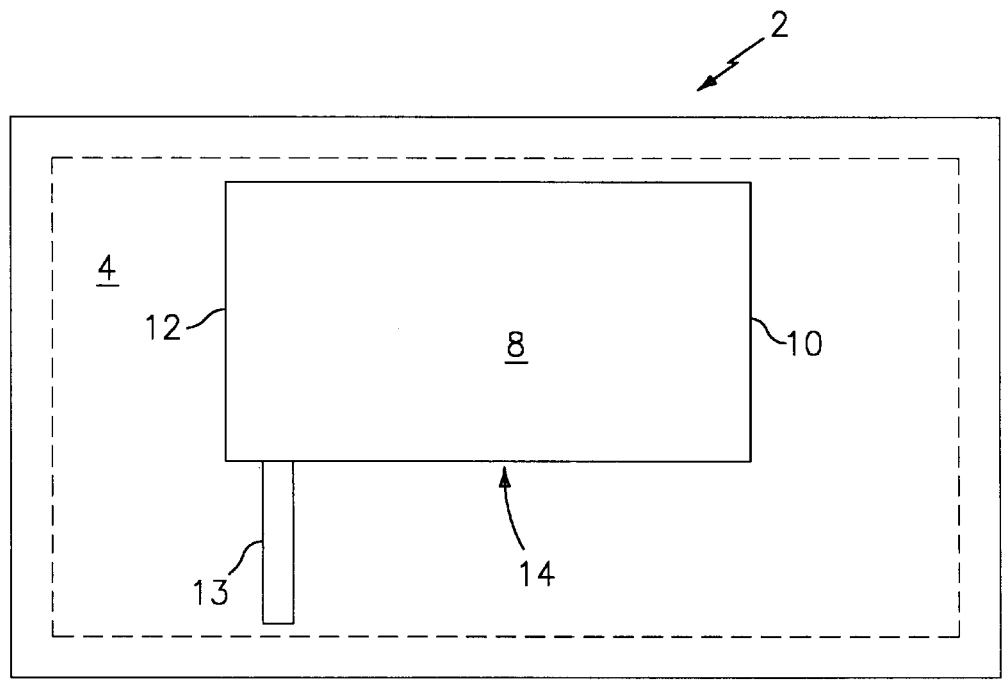
FIG. 3 is a plan view of a sample chamber similar to that shown in FIG. 1 but which is provided with a second embodiment of an instrument calibration area associated with the chamber.

FIG. 3 shows a device 2 formed in accordance with this invention which includes a second embodiment of an onboard structure which can be used to calibrate the instrument so that it can determine chamber field of view thicknesses after being calibrated during use of the instrument by the technician. In the embodiment shown in FIG. 3, a rectangular glass capillary 13 of known volume and preferably of about $20\mu$ thickness is contiguous with the thicker end region 12 of the chamber 14, whereby the capillary 13 will fill with the sample, and with the admixed colorant. After red cell rouleaux forms within the capillary 13, the average plasma fluorescence from lacunae in the capillary 13 can be determined by the methods described above. The volume-per-unit-length of the capillary 13 is known since it is manufactured to a precise tolerance, thus the fluorescence per volume can be calculated by the scanning instrument.

Figure 4:
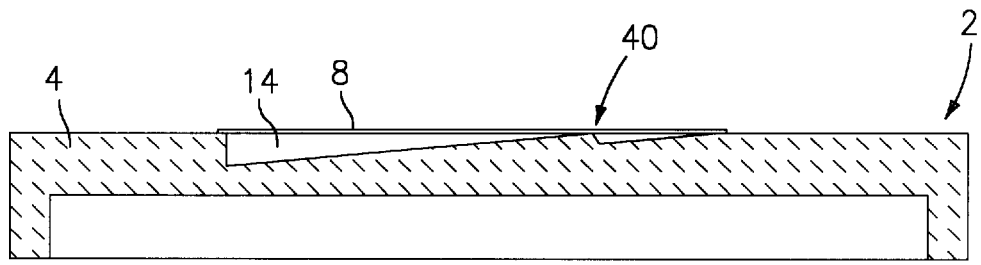
FIG. 4 is a cross sectional view of one embodiment of a sample chamber which has a through plane thickness that varies in different X, Y regions of the chamber, and which chamber has a third embodiment of an instrument calibration area associated with it.
Figure 5:
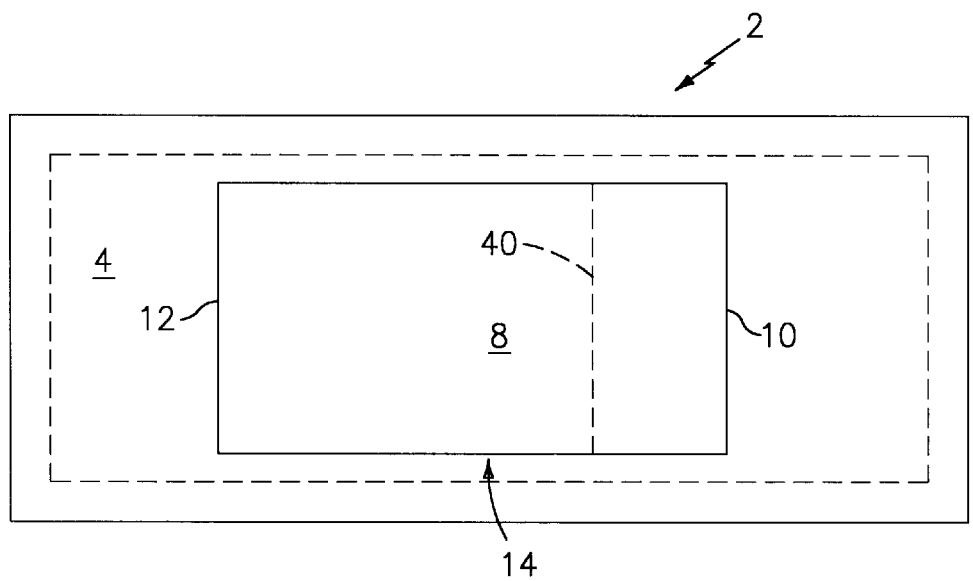
FIG. 5 is a plan view of the instrument calibration area of FIG. 4.

FIGS. 4 and 5 show an embodiment which is similar to that of FIG. 1, except that the known geometric feature is a continuous step 40 of known height which transverses at least a part of the chamber. To perform the calibration measurement, the average fluid colorant intensity readings are performed on either side of the step 40, and the mean differences between the readings on one side versus the other represent the change in magnitude of the colorant signal for a given chamber thickness. Again, because the area of the field is known, this height reading can be translated into volume, or vice versa. The step 40 may be abrupt or may be gradual as long as it provides an adequate demarcation for the instrument to locate properly.

Figure 6:
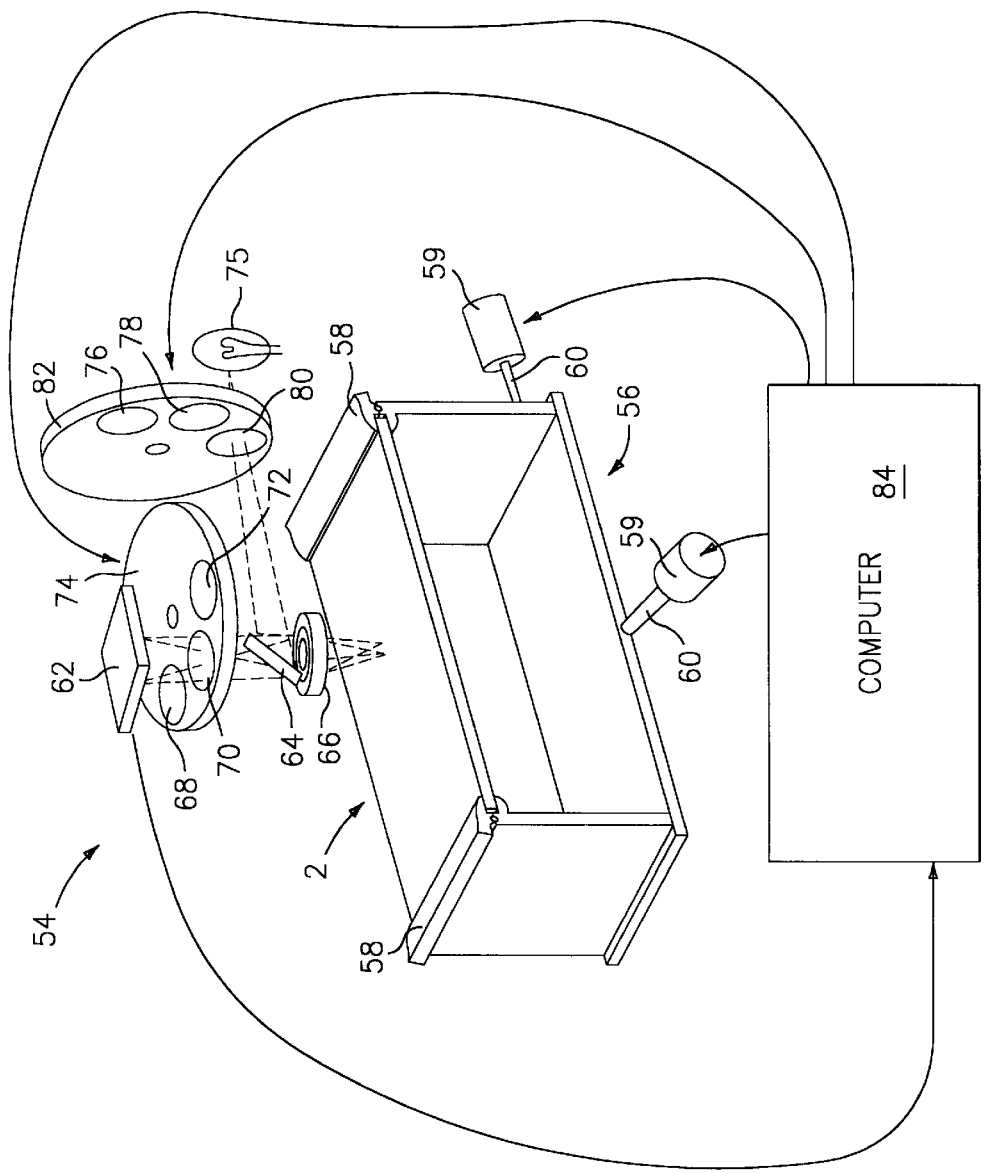
FIG. 6 is a schematic view of a scanning instrument which can be used to analyze the sample in the container.

FIG. 6 is a schematic depiction of an automated colorimetric microscopical instrument assembly which is described in greater detail in co-pending U.S. patent application Attorney's Docket No. UFB-017. The instrument assembly is denoted generally by the numeral 54, and it can be used to scan a blood sample that is contained in the device 2, and can, without significant human intervention, colorometrically analyze wavelengths of color emissions from different white cell types and reticulocytes in the blood sample, thereby identifying these cell types. It can also perform per-unit-blood sample volume counts of the various white cell types and reticulocytes in the blood sample. The instrument assembly 54 is designed to create and store or transmit the images of different white cells and reticulocytes in the blood sample being scanned. The instrument assembly 54 includes a stage 56 which includes clips 58 which engage the sample holder 2, and enables the sample holder 2 to be moved transversely in the X and Y directions as the contents of the sample holder 2 are scanned.

Reversible electric motors 58 can be used to selectively rotate drive screws 60 in opposite directions so that the sample holder 2 can be transversely moved in the X and Y directions. In this manner, the entire contents of the sample holder 2 can be scanned. The automatic embodiment of the disclosed instrument assembly 54 includes a CCD camera 62, a beam splitter 64, and lens 66 set which can be selectively moved in the Z direction so as to focus upon the sample-containing portions in the sample holder assembly 2. The CCD camera 62 may view and record images of the sample through a plurality of different emission light wave filters 68, 70 and 72 which may be mounted on a selectively rotatable filter wheel 74. The instrument assembly 54 also includes an excitation light source 75 which directs an excitation light beam at the sample holder 2 through the beam splitter 64 and the focusing lens set 66. A series of excitation light wave length filters 76, 78 and 80 may be mounted on a selectively rotatable filter wheel 82. The excitation light beam is deflected by the beam splitter 64 toward the focusing lens 66, and is focused on the sample holder 2 by the lens 66. Thus, the two filter wheels 74 and 82 can allow one to selectively control and vary the wave lengths of the excitation light source, as well as the emitted light source. A pre-programmed processor controller 84 is operable to selectively control movement of the sample holder 2; the rotation of the filter wheels 74 and 82; and operation of the CCD camera 62. The controller 84 thus enables fully automatic operation of the instrument assembly 12 without the need of significant human intervention.

While a fluorescent marker is preferred, a dye which absorbs transmitted light can also be used. When such a dye is used, the values of the optical signal density are measured rather than the fluorescent signal intensity.

Since many changes and variations of the disclosed embodiments of the invention may be made without departing from the inventive concept, it is not intended to limit the invention otherwise than as required by the appended claims.

I claim:

1. A method for calibrating a chamber held within an optical scanning instrument so as to enable the instrument to determine volumes of fields of view, or volumes of formed constituents contained in a biological fluid which fluid includes a clear carrier liquid in which the formed constituents in the fluid are suspended, said method comprising:

a) the step of providing a container for receiving a quiescent sample of the biological fluid, said container including a sample-receiving sample-viewing chamber which has regions therein of indeterminate varying through plane thicknesses;

b) the step of introducing a mixture of a colorant and the biological fluid sample into the chamber and allowing the mixture of colorant and biological fluid sample to spread out in the chamber so as to form a quiescent colored biological fluid sample layer that fills the chamber, said colored biological fluid sample layer including colored regions which include the formed constituents along with colored formed constituent-free portions of the clear carrier liquid;

c) the step of providing a calibration area having a known through plane volume or depth, which calibration area is associated with the chamber in a manner which enables a fraction of the colored clear carrier liquid to enter into and fill the calibration area in the container;

d) the step of communicating said known through plane volume or depth in said calibration area to the scanning instrument; and e) the step of scanning said calibration area with said instrument in order to quantify a degree of colorant signal intensity emanating from said calibration area so as to enable the instrument to identify and store a colorant signal intensity-to-chamber depth relationship for the container being scanned, thereby enabling the instrument to ascertain depths of subsequent fields of view scanned as a function of color signal intensity emanating from varying depth regions of the sample chamber.

2. The method of claim 1 wherein said calibration area includes a geometric feature of known volume, which feature is operable to alter a colorant signal emanating from a portion of the calibration area which contains the geometric feature to a degree which is proportional to the volume of the geometric feature, said method including:

f) the step of communicating said known geometric feature volume to the scanning instrument; and g) the step of scanning said geometric feature in said calibration area with said instrument in order to quantify a degree of colorant signal intensity emanating from said calibration area so as to enable the instrument to identify and store a colorant signal intensity change-to-geometric feature volume relationship for the container being scanned, thereby enabling the instrument to ascertain volumes of formed constituents contained in subsequent fields of view scanned as a function of color signal intensity emanating from regions in the chamber which contain formed constituents in the sample.

3. The method of claim 1 wherein said calibration area is a capillary tube of known volume which capillary tube communicates with the chamber.

4. The method of claim 2 wherein said calibration area is a well of known depth which well communicates with the chamber.

5. The method of claim 4 wherein said geometric feature is contained in said well.

6. The method of claim 5 wherein said geometric feature is a protuberance formed on a bottom wall of said well.

7. A method for calibrating an optical scanning instrument so as to enable the instrument to determine volumes of formed constituents contained in a biological fluid which fluid includes a clear carrier liquid in which the formed constituents in the fluid are suspended, said method comprising:

a) the step of providing a container for receiving a quiescent sample of the biological fluid, said container including a sample-receiving sample-viewing chamber which has regions therein of indeterminate varying through plane thicknesses;

b) the step of introducing a mixture of a colorant and the biological fluid sample into the chamber and allowing the mixture of colorant and biological fluid sample to spread out in the chamber so as to form a quiescent colored biological fluid sample layer that fills the chamber, said colored biological fluid sample layer including colored regions which include the formed constituents along with colored formed constituent-free portions of the clear carrier liquid;

c) the step of providing a calibration area that contains a geometric feature of known volume, which feature is operable to alter a colorant signal emanating from a portion of the calibration area which contains the geometric feature to a degree which is proportional to the volume of the geometric feature, said calibration area being associated with the chamber in a manner which enables a fraction of the colored clear carrier liquid to enter into and fill the calibration area in the container;

d) the step of communicating said known geometric feature volume to the scanning instrument; and e) the step of scanning said geometric feature in said calibration area with said instrument in order to quantify a degree of colorant signal intensity emanating from said calibration area so as to enable the instrument to identify and store a colorant signal intensity-decrement-to-geometric feature volume relationship for the container being scanned, thereby enabling the instrument to ascertain volumes of formed constituents contained in subsequent fields of view scanned as a function of color signal intensity emanating from regions in the chamber which contain formed constituents in the sample.

8. A sample container having an area which is useful for calibrating an optical scanning instrument, so as to enable the scanning instrument to determine volumes of fields of view, or volumes of formed constituents contained in a biological fluid sample which sample includes a clear carrier liquid, and which biological fluid is being analyzed in the container, said container comprising:

a) a sample-receiving and sample-viewing chamber which has regions therein of indeterminate varying through plane thicknesses; and b) a calibration area of known through plane thickness or volume, which calibration area is associated with the chamber in a manner which enables a fraction of the colored clear carrier liquid to enter into and fill the calibration area in the container, whereby a degree of color signal intensity emanating from said calibration is proportional to said known through plane depth or volume of said calibration area.

9. The sample container of claim 8 further comprising a geometric feature of known volume in a portion of said calibration area, said feature being operable to alter the colorant signal emanating from the portion of the calibration area which contains the geometric feature to a degree which is proportional to the volume of the geometric feature.

10. The sample container of claim 8 further comprising a capillary tube which contains the calibration area.

* * * * *